(12) United States Patent
Chen

(10) Patent No.: US 10,197,447 B2
(45) Date of Patent: Feb. 5, 2019

(54) COLOR RECOGNITION DEVICE AND COLOR RECOGNITION METHOD

(71) Applicant: BOE TECHNOLOGY GROUP CO., LTD., Beijing (CN)

(72) Inventor: Shuo Chen, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 15/533,299

(22) PCT Filed: Jun. 28, 2016

(86) PCT No.: PCT/CN2016/087440
§ 371 (c)(1),
(2) Date: Jun. 5, 2017

(87) PCT Pub. No.: WO2017/152547
PCT Pub. Date: Sep. 14, 2017

(65) Prior Publication Data
US 2018/0106679 A1    Apr. 19, 2018

(30) Foreign Application Priority Data

Mar. 8, 2016  (CN) .......................... 2016 1 0131326

(51) Int. Cl.
*G01N 21/25*    (2006.01)
*G01J 3/50*    (2006.01)
(Continued)

(52) U.S. Cl.
CPC .............. *G01J 3/50* (2013.01); *G01J 3/0264* (2013.01); *G01J 3/10* (2013.01); *G01J 3/463* (2013.01);
(Continued)

(58) Field of Classification Search
CPC ...... G01J 3/51; G01J 3/513; G01J 3/50; G01J 3/46; G01J 3/02
(Continued)

(56) References Cited

U.S. PATENT DOCUMENTS

| 2007/0196095 A1* | 8/2007 | Perala | G03B 15/03 396/155 |
| 2013/0002531 A1* | 1/2013 | Krahenbuhl | G06F 3/041 345/156 |
| 2017/0148189 A1* | 5/2017 | Li | G06T 7/90 |

FOREIGN PATENT DOCUMENTS

| CN | 2716820 Y | 8/2005 |
| CN | 1916576 A | 2/2007 |

(Continued)

OTHER PUBLICATIONS

First Chinese Office Action, for Chinese Patent Application No. 201610131326.7, dated Nov. 6, 2017, 21 pages.
International Search Report and Written Opinion dated Dec. 9, 2016, for corresponding PCT Application No. PCT/CN2016/087440.

*Primary Examiner* — Md M Rahman
(74) *Attorney, Agent, or Firm* — Kinney & Lange, P.A.

(57) ABSTRACT

The present disclosure provides a color recognition device and a color recognition method, and belongs to the technical field of color recognition. In an embodiment, the color recognition device includes a head portion and a main body portion; the head portion has a groove in which a sensor module configured to capture color information of the object to be detected is disposed; and the main body portion includes: a storage module configured for storing standard color parameters of a variety of colors, and a central processing unit configured for comparing color information of the object to be detected with the standard color param-
(Continued)

eters of the variety of colors stored in the storage module, to recognize color of the object to be detected.

16 Claims, 4 Drawing Sheets

(51) Int. Cl.
    *G01J 3/10*     (2006.01)
    *G01V 8/14*     (2006.01)
    *G01J 3/02*     (2006.01)
    *G01J 3/46*     (2006.01)
    *G01J 3/51*     (2006.01)
    *G01J 3/52*     (2006.01)

(52) U.S. Cl.
    CPC ................. *G01J 3/51* (2013.01); *G01J 3/524* (2013.01); *G01N 21/251* (2013.01); *G01V 8/14* (2013.01); *G01J 2003/466* (2013.01)

(58) Field of Classification Search
    USPC .......................................................... 356/406
    See application file for complete search history.

(56) References Cited

FOREIGN PATENT DOCUMENTS

| | | | |
|---|---|---|---|
| CN | 101109659 A | * | 1/2008 |
| CN | 201130057 Y | | 10/2008 |
| CN | 201540164 U | | 8/2010 |
| CN | 101403741 B | | 7/2012 |
| CN | 202693478 U | | 1/2013 |
| CN | 204740069 U | | 11/2015 |
| CN | 204832014 U | | 12/2015 |
| CN | 105606542 A | | 5/2016 |
| CN | 205506668 U | | 8/2016 |
| JP | 2005257374 A | | 9/2005 |
| WO | 2004079314 A1 | | 9/2004 |
| WO | WO 2004079314 A1 | * | 9/2004 ................ G01J 3/50 |
| WO | 2015100208 A2 | | 7/2015 |

* cited by examiner

US 10,197,447 B2

COLOR RECOGNITION DEVICE AND COLOR RECOGNITION METHOD

CROSS-REFERENCE TO RELATED APPLICATION

This application claims the benefit of Chinese Patent Application No. 201610131326.7 filed on Mar. 8, 2016 in the State Intellectual Property Office of China, the whole disclosure of which is incorporated herein by reference.

BACKGROUND

1. Technical Field

The present disclosure generally relate to the field of color recognition technology, and particularly to a color recognition device and a color recognition method.

2. Description of the Related Art

Color recognition device has been rapid developed with the progress of science and technology. Color recognition work, in which human eyes play a leading role in the past, in the process of production has been replaced gradually by color recognition device. For example, the color recognition device may be adopted for material sorting, brand recognition, image processing, product quality inspection, vehicle identification and so on.

Conventional color recognition device is mainly consisted of a tray, a color detector and a data processing unit. A color recognition process in which such color recognition device is adopted is as follows.

(1) An object to be detected is placed on the tray.
(2) The color detector emits a detection light signal to the object to be detected on the tray, receives a reflected light signal emitted from the object to be detected, converts the received reflected light signal into electrical signal, and transmits the obtained electrical signal to the data processing unit.
(3) The data processing unit receives the electrical signal, performs a comparison calculation between the electrical signal and a variety of stored color parameters, and generates a color recognition result.

SUMMARY

In accordance with a first aspect of embodiments of the present disclosure, there is provided a color recognition device, the device comprises a head portion and a main body portion;

the head portion has a groove in which a sensor module configured to capture color information of the object to be detected is disposed; and the main body portion comprises: a storage module configured for storing standard color parameters of a variety of colors, and a central processing unit configured for comparing color information of the object to be detected with the standard color parameters of the variety of colors stored in the storage module, to recognize color of the object to be detected.

In an embodiment of the present disclosure, the groove is provided therein with a light source configured to offer brightness to the object to be detected in the state of a darkroom which is formed when the groove is in contact with the object to be detected.

In an embodiment of the present disclosure, the light source comprises a standard white-color light source.

In an embodiment of the present disclosure, the sensor module comprises an imaging unit, a color filtering unit and a color processing unit; the imaging unit is configured to perform an imaging process on the object to be detected;

the color filtering unit is configured to separate color in an image of the object to be detected into red, green and blue gray scale brightness; and the color processing unit is configured to capture values of the gray scale brightness in the image of the object to be detected.

In an embodiment of the present disclosure, the imaging unit comprises a lens.

In an embodiment of the present disclosure, the color filtering unit comprises a CMOS (Complementary Metal Oxide Semiconductor) sensor.

In an embodiment of the present disclosure, the main body portion further comprises a communication module and a power module;

the communication module is configured to transmit the color information of the object to be detected to an upper computer; and the power module is configured to supply the power to the device.

In an embodiment of the present disclosure, the communication module comprises one of a Bluetooth module, a Wi Fi (wireless fidelity) module, an infrared module and a NFC (Near Field Communication) module.

In an embodiment of the present disclosure, the power module comprises a battery cell and a power management unit.

In an embodiment of the present disclosure, the device further comprises: a standard white board configured to correct the color information of the object to be detected when the object to be detected is in the state of non-darkroom.

In accordance with a second aspect of the present disclosure, there is provided a color recognition method, characterized in that, the method is applied to the color recognition device in accordance with the above first aspect, and the method comprises the following steps of:

capturing, by the sensor module, color information of the object to be detected;

judging, by the central processing unit, whether or not there is ambient light in the groove; and acquiring, by the central processing unit, standard color parameters of a variety of colors pre-stored in the storage module, and, comparing, by the central processing unit, color information of the object to be detected with the standard color parameters of the variety of colors, to obtain a color recognition result.

In an embodiment of the present disclosure, the step of capturing, by the sensor module, color information of the object to be detected, further comprises:

performing, by the imaging unit, an imaging process on the object to be detected;

separating, by the color filtering unit, color in an image of the object to be detected into red, green and blue gray scale brightness; and capturing, by the color processing unit, values of the gray scale brightness in the image of the object to be detected.

In an embodiment of the present disclosure, before the step of comparing, by the central processing unit, the color information of the object to be detected with the standard color parameters of the variety of colors, to obtain a color recognition result, the method further comprises the following steps of:

converting, by the central processing unit, the color information of the object to be detected into a digital signal; and comparing, by the central processing unit, the color information of the object to be detected with the standard color parameters of the variety of colors, to obtain the color recognition result.

In an embodiment of the present disclosure, after the step of judging, by the central processing unit, whether or not there is ambient light in the groove, the method further comprises the following steps of:

if there is no ambient light in the groove, acquiring, by the central processing unit, standard color parameters of the variety of colors pre-stored in the storage module, and, directly comparing the color information of the object to be detected with the standard color parameters of the variety of colors, to obtain the color recognition result; or if there is ambient light in the groove, capturing, by the sensor module, color information of the standard white board in the current condition; correcting, by the central processing unit, the color information of the object to be detected in accordance with the color information of the standard white board; and, comparing, by the central processing unit, the corrected color information with the standard color parameters of the variety of colors, to obtain the color recognition result.

In an embodiment of the present disclosure, the method further comprises the following step of:

transmitting, by the communication module, the color recognition result to the upper computer.

BRIEF DESCRIPTION OF THE DRAWINGS

In order to provide a more clear explanation of technical solutions according to embodiments of the present invention, there is provided a brief introduction of the attached drawings used in the following description of the embodiments. Obviously, the drawings mentioned in the following description merely belong to some embodiments of the present invention. However, for those skilled in the art, other drawings may be achieved on the basis of these attached drawings without involving any inventive steps.

DETAILED DESCRIPTION OF THE EMBODIMENTS

In order to provide a more clear understanding of objects, technique solutions and advantages of embodiments of the present disclosure, the embodiments of the present disclosure will be further described hereinafter in detail and completely with reference to the attached drawings.

The inventor(s) have found that at least one of the following problems exists in implementing a color recognition process by conventional color recognition device. A tray is required to be provided in conventional color recognition device, which leads to poor portability. Moreover, the detection process encounters certain limitations since it depends on the detection light and the reflected light. In addition, the detection process causes greater consumption of resources.

Figure 1:
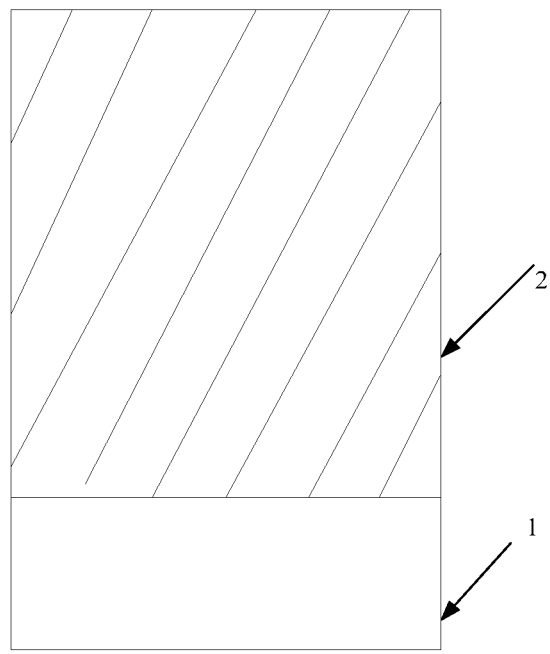
FIG. 1 is a schematic view of a structure of a color recognition device according to an embodiment of the present disclosure.

A color recognition device is provided according to an embodiment of the present disclosure. Referring to FIG. 1, the device adopts a pencil-shaped design and includes a head portion 1 and a main body portion 2.

Figure 2:
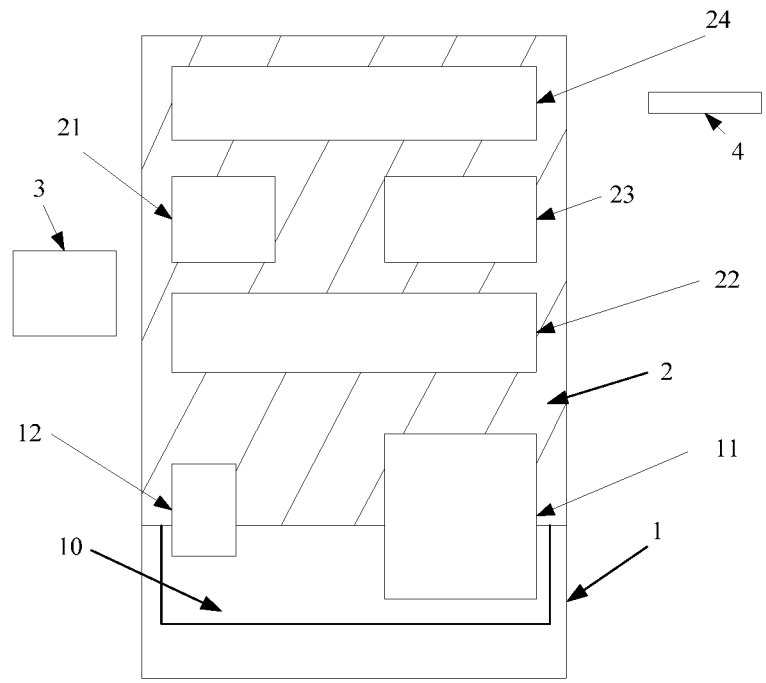
FIG. 2 is a schematic view of a structure of components and parts in a color recognition device according to another embodiment of the present disclosure.

Referring to FIG. 2, the head portion 1 has a groove 10 in which a sensor module 11 configured to capture color information of the object to be detected is disposed. The main body portion 2 comprises a storage module 21 and a central processing unit 22. The storage module 21 is configured for storing standard color parameters of a variety of colors, and the color parameters may be R (Red), G (Green), B (Blue) three color channels each of which possesses gray scale brightness values of 0-255. The central processing unit 22 is configured for comparing color information of the object to be detected with the standard color parameters of the variety of colors stored in the storage module 21, to recognize color of the object to be detected. For example, the standard color parameters of the variety of colors stored in the storage module 21 may be presented in Table 1 as follows.

TABLE 1

| Common Colors | Color Parameters | | |
| --- | --- | --- | --- |
|  | R | G | B |
| Black | 0 | 0 | 0 |
| Blue | 0 | 0 | 255 |
| Green | 0 | 255 | 0 |
| Cyan | 0 | 255 | 255 |
| Red | 255 | 0 | 0 |
| Carmine | 255 | 0 | 255 |
| Yellow | 255 | 255 | 0 |
| White | 255 | 255 | 255 |

Referring to FIG. 2, the groove 10 is also provided therein with a light source 12. The light source 12 is preferably a standard white-color light source and is configured to offer brightness to the object to be detected in the state of a darkroom which is formed when the groove 10 is in contact with the object to be detected, so that the sensor module 11 is able to capture the color information of the object to be detected.

Figure 3:
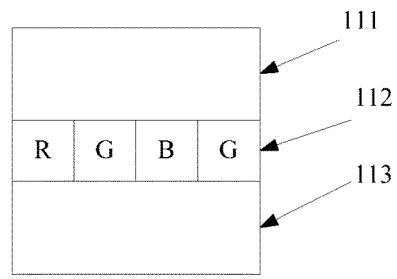
FIG. 3 is a schematic view of a structure of a sensor module in a color recognition device according to another embodiment of the present disclosure.

Referring to FIG. 3, the sensor module 11 comprises an imaging unit 111, a color filtering unit 112 and a color processing unit 113. The imaging unit 111 may be lens or the like, and is configured to perform an imaging process on the object to be detected, so that the color filtering unit 112 can acquire an image of the object to be detected. The color filtering unit 112 may be a multicolor filtering sheet and the like, and is configured to separate color in the image of the object to be detected into red (R), green (G) and blue (B) gray scale brightness. The color processing unit 113 may be a CMOS sensor, and is configured to capture, after color in the image of the object to be detected is separated by the color filtering unit into red (R), green (G) and blue (B) gray scale brightness, values of the gray scale brightness in the image of the object to be detected. The color processing unit 13 is also configured to convert the values of the gray scale brightness in the image of the object to be detected from analog signals into digital signals, so that the color information of the object to be detected is easily analyzed by the central processing unit 21.

Referring to FIG. 2, the main body portion 2 further may comprise a communication module 23 and a power module 24. The communication module may be one of a Bluetooth module, a Wi Fi module, an infrared module, a Near Field Communication NEC module and the like. The communication module 23 can be in communication with an upper computer 4, and transmit the color information of the object to be detected to the upper computer during communication. The power module 24 is configured to supply the power to the whole color recognition device. The power module 24 may comprise a battery cell configured for storage of electrical power and a power management unit configured to manage power supply of the battery cell, for example, to manage charging and discharging of the battery cell and so on.

In this embodiment, the color recognition device may further comprise a standard white board 3, which is independent of the head portion 1 and the main body portion 2, and which is configured to correct the color information of the object to be detected when the object to be detected is in the state of non-darkroom, so as to avoid a result of the detection from being interfered by ambient light.

In this embodiment, besides having the abovementioned functions, the central processing unit 12 is also able to convert CMOS signals in the color processing unit 113 into digital signals of red (R), green (G) and blue (B), and to control operations of these functional modules in the color recognition device, for example, to control power supply of the power module 24 to whole device, to control communication between the communication module 23 and the upper computer, and so on.

Figure 4:
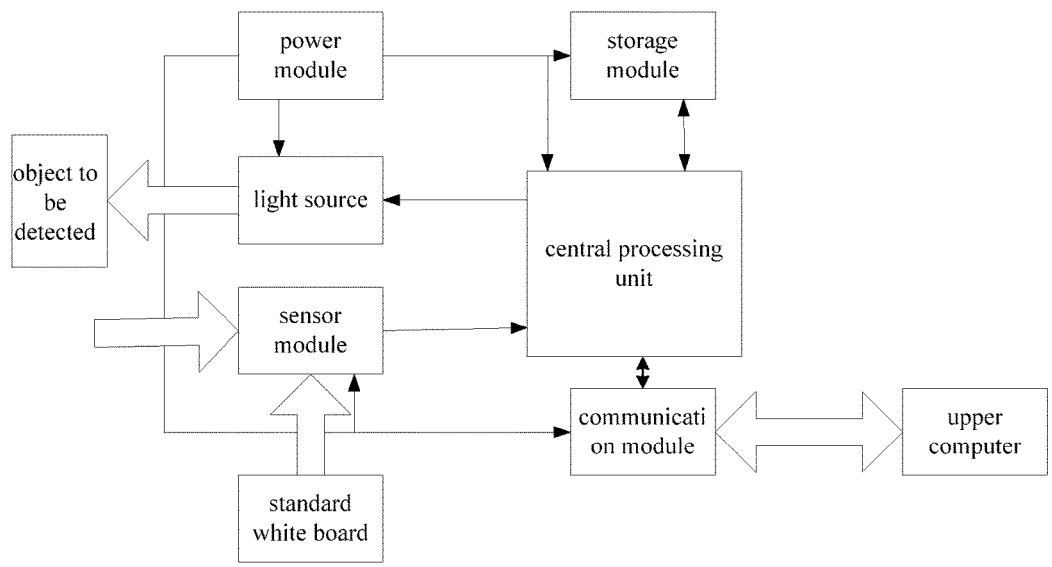
FIG. 4 is a functional block diagram of a color recognition device according to another embodiment of the present disclosure.

FIG. 4 is a functional block diagram of a color recognition device according to an embodiment of the present disclosure. It can be seen from FIG. 4, when the groove 10 of the head portion of the color recognition device gets into contact with an object to be detected to create a darkroom, the light source 12 illuminates the object to be detected. The sensor module 1 captures color information of the object to be detected, and transmits the color information of the object to be detected to the central processing unit 22. The central processing unit 22 obtains standard color parameters of a variety of colors from the storage module 21, and compares the color information of the object to be detected with the standard color parameters of the variety of colors so as to recognize color of the object to be detected. When no darkroom is created between the groove 10 of the head portion of the color recognition device and an object to be detected, the object to be detected is in the state of non-darkroom. The sensor module 1 captures color information of the object to be detected and color information of the standard white board, and transmits the color information of the object to be detected and the color information of the standard white board to the central processing unit 22. The central processing unit 22 obtains standard color parameters of a variety of colors from the storage module 21, and corrects the color information of the object to be detected in accordance with the color information of the standard white board, so as to recognize color of the object to be detected. The communication module 23 transmits the recognized color of the object to be detected to the upper computer. In the above process, the power module 24 can supply electricity to the storage module 21, the central processing unit 22, the sensor module 11, the light source 12 and the communication module 23, to ensure normal operation of the color recognition device.

The color recognition device according to embodiments of the present disclosure adopts a pencil-shaped design. The head portion of the device is provided with the sensor module configured to capture color information of an object. It can recognize directly color of the object to be detected, without requiring provision of the tray and depending on the detection light and the emission light. Accordingly, it not only improves portability but also reduces resource consumption during detection.

Figure 5:
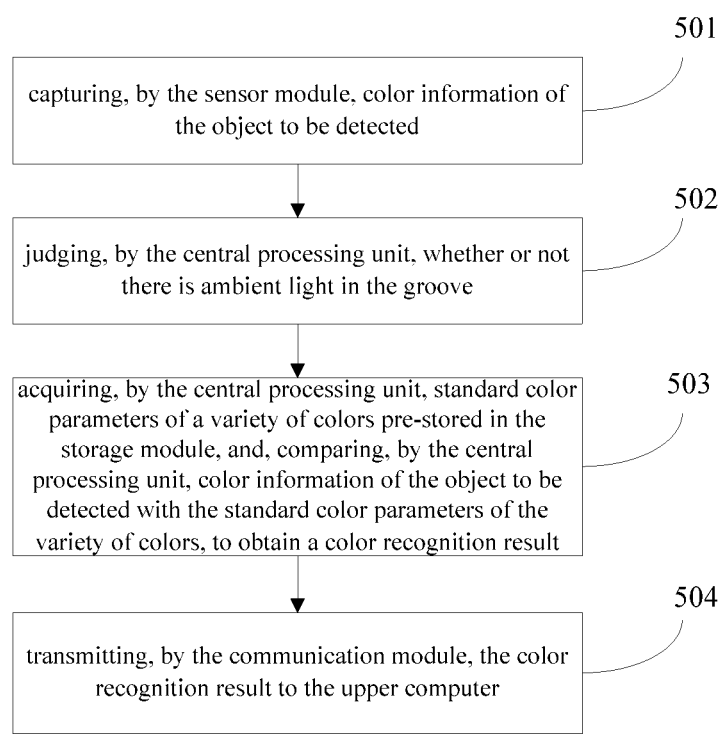
FIG. 5 is a flow diagram of a color recognition method according to an embodiment of the present disclosure.

A color recognition method, which can be applied to the color recognition device according to any one of the embodiments shown in FIG. 1 to FIG. 4, is provided according to an embodiment of the present disclosure. Referring to FIG. 5, the color recognition method according to this embodiment comprises the following steps.

A step 501 is to capture, by the sensor module, color information of the object to be detected;

a step 502 is to judge, by the central processing unit 22, whether or not there is ambient light in the groove 10; and a step 503 is to acquire, by the central processing unit 22, standard color parameters of a variety of colors pre-stored in the storage module 21, and, compare color information of the object to be detected with the standard color parameters of the variety of colors, to obtain a color recognition result.

Regarding the step 501, namely, to capture, by the sensor module, color information of the object to be detected, in an embodiment, the color information of the object to be detected is consisted of different gray scale brightness values, of 0-255, possessed in red (R), green (G), blue (B) three color channels. In this embodiment, as shown in FIG. 3, the sensor module 10 comprises an imaging unit 111, a color filtering unit 112 and a color processing unit 113. Based on functions of the imaging unit 111, the color filtering unit 112 and the color processing unit 113, the sensor module 11 captures color information of the object to be detected (namely the step 501) in the following sub-steps.

A first sub-step is to perform, by the imaging unit 111, an imaging process on the object to be detected, so as to obtain an image of the object to be detected.

A second sub-step is to separate, by the color filtering unit 112, color in the image of the object to be detected into red (R), green (G) and blue (B) gray scale brightness.

A third sub-step is to capture, by the color processing unit 113, values of the gray scale brightness in the image of the object to be detected, so as to obtain the color information of the object to be detected.

After capturing the color information of the object to be detected, the sensor module 11 transmits the color information of the object to be detected to the central processing unit 22, so that the central processing unit 22 recognizes color of the object to be detected by analyzing the color information of the object to be detected.

Regarding the step 502, namely, to judge, by the central processing unit 22, whether or not there is ambient light in the groove 10.

In this embodiment, when the color recognition device is adopted to perform a color recognition on an object to be detected, color of the object to be detected can be recognized under the state of a darkroom formed by contacting the groove 10 with surface of the object to be detected. In this case, there is no ambient light in the groove 10, and it is needed to turn on the light source 12 so as to bring brightness to the object to be detected. Color information captured by the sensor module 11 from the object to be detected is actually the color information of the object to be detected itself. When the color recognition device is adopted to perform a color recognition on an object to be detected, color of the object to be detected can also be recognized under the state that no darkroom is formed by the groove 10 and surface of the object to be detected. In this case, color information captured by the sensor module 11 from the object to be detected includes not only the color information of the object to be detected itself, but also color information of the ambient light. Since the fact that whether or not there is ambient light in the groove affects directly what recognition method, of recognizing color of an object to be detected, is adopted by the central processing unit 22, the central processing unit 22 needs to judge whether or not there is ambient light in the groove 10 before recognizing color information of an object to be detected.

In order to judge, by the central processing unit 22, whether or not there is ambient light in the groove 10, whether the light source 12 is turned on or not may be detected. If the light source 12 is detected to be in a turned-on state, it is judged that there is no ambient light in the groove 10. Conversely, if the light source 12 is detected to be in a turned-off state, it is judged that there is ambient light in the groove 10.

Regarding the step 503, namely, to acquire, by the central processing unit 22, standard color parameters of a variety of colors pre-stored in the storage module 21, and, compare color information of the object to be detected with the standard color parameters of the variety of colors, to obtain a color recognition result.

In the step 503, if it is judged that there is no ambient light in the groove 10, color information captured by the sensor module 11 from the object to be detected is actually the color information of the object to be detected itself. In this case, the central processing unit 22 can directly acquire standard color parameters of a variety of colors from the storage module, and directly compare the color information of the object to be detected with the standard color parameters of the variety of colors, to choose a color, which corresponds to a color parameter that is the same as color information of the object to be detected, as the color of the object to be detected.

In order to ensure smooth performing of the recognition process, before comparing the color information of the object to be detected with the standard color parameters of the variety of colors, the central processing unit 22 converts the color information of the object to be detected into digital signal. As a result, when the color information of the object to be detected is compared with the standard color parameters of the variety of colors, the central processing unit 22 can compare the standard color parameters of a variety of colors with the digital signal, to obtain a color recognition result.

In the step 503, if it is judged that there is ambient light in the groove 10, in order to improve accuracy of color recognition on color of the object to be detected, the method according to the present embodiment further performs the recognition in conjunction with a standard white board. The specific recognition process includes the following sub-steps (1)-(3).

(1) The sensor module 11 captures color information of the standard white board under the ambient light.

Specific process of the capturing step is the same as that of capturing color information of the object to be detected. For the details, please refer to the description on the process of capturing color information of the object to be detected, and it will not be described here.

(2) The central processing unit 22 corrects the color information of the object to be detected in accordance with the color information of the standard white board.

For the details of the correcting, in the central processing unit 22, the color information of the object to be detected is subtracted with the color information of the standard white board. Of course, the details of correcting, by the central processing unit 22, the color information of the object to be detected in accordance with the color information of the standard white board are not limited in this embodiment, and other manners may be adopted.

(3) The central processing unit 22 compares the corrected color information with the standard color parameters of the variety of colors, to obtain the color recognition result.

For the details of the comparing, the central processing unit 22 may firstly convert the corrected color information into digital signal, next, compare the digital signal converted from the corrected color information with the standard color parameters of the variety of colors, and then, choose a color, which corresponds to a color parameter that is the same as color information of the object to be detected, as the color of the object to be detected.

In addition, the method according to the present embodiment may further comprise a step 504, namely, to transmit, by the communication module 23, the color recognition result to the upper computer.

In the step 504, in order to allow a user to learn promptly the color of the object to be detected, after the central processing unit 22 recognizes the color information of the object to be detected, the communication module 23 further transmits the color recognition result to the upper computer for displaying. From the color recognition result displayed in the upper computer, the user can learn the color of the object to be detected.

The abovementioned color recognition process will be described and explained by taking these shown in FIG. 6 as an example, in order to ease the understanding.

Figure 6:
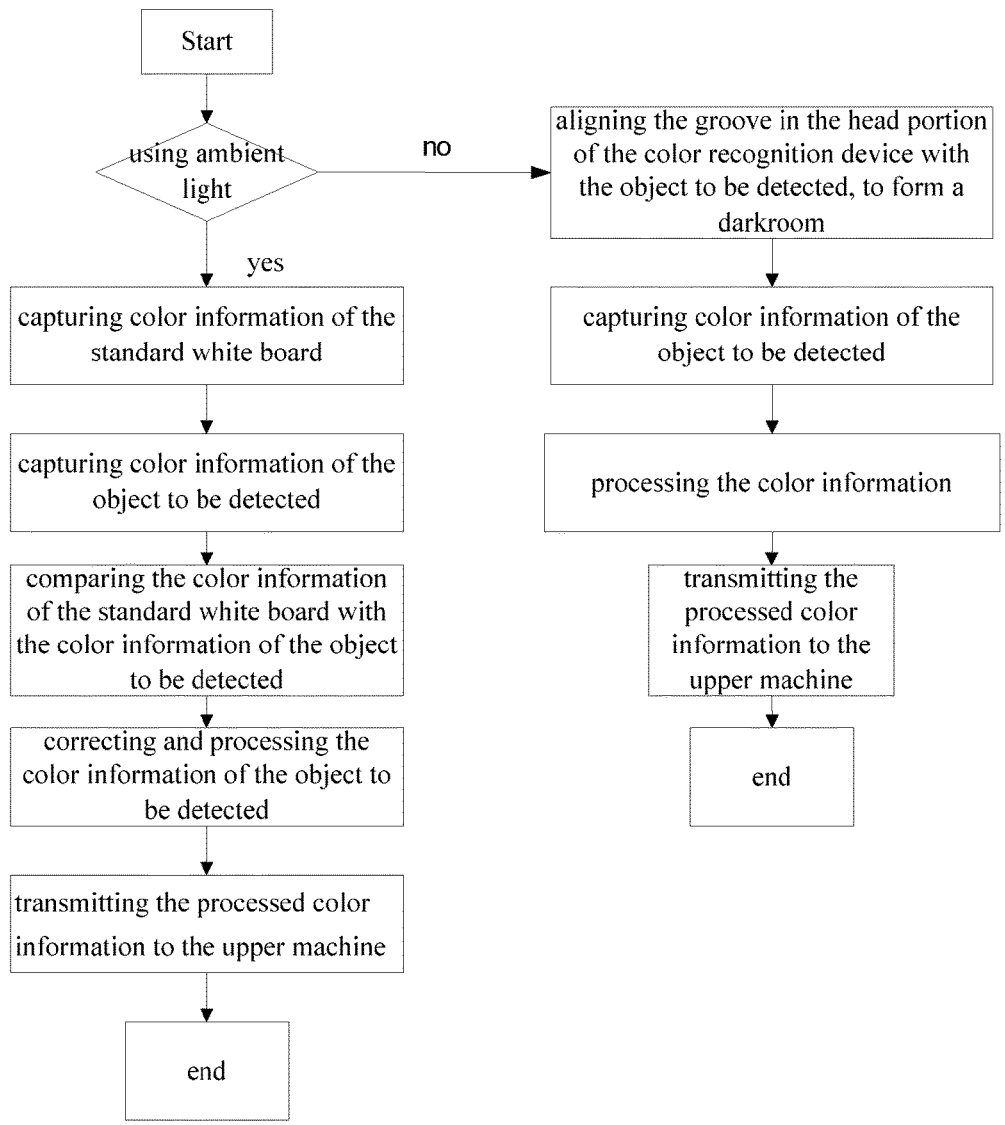
FIG. 6 is a flow diagram of a color recognition process according to another embodiment of the present disclosure.

Referring to FIG. 6, when the color recognition device is used to recognize color of an object to be detected, if the detection is implemented without ambient light, the groove 10 in the head portion of the color recognition device is aligned with the object to be detected, to form a darkroom. In the state of darkroom, the light source is turned on to illuminate the object to be detected, and the sensor module captures color information of the object to be detected, and transmits the color information of the object to be detected to the central processing unit. The central processing unit converts the color information of the object to be detected into digital signal, and then compares the color information of the object to be detected with the standard color parameters of the variety of colors stored in the storage module, to obtain the color recognition result. After that, the recognition result is transmitted to the upper computer. If the detection is implemented with the ambient light, the sensor module needs to capture color information of the standard white board and captures color information of the object to be detected, and then transmits color information of the standard white board and color information of the object to be detected to the central processing unit. The central processing unit corrects the color information of the object to be detected in accordance with the color information of the standard white board, and compares the corrected color information of the object to be detected with the standard color parameters of the variety of colors stored in the storage module, to obtain the color recognition result. After that, the color recognition result is transmitted to the upper computer.

In the color recognition method according to embodiments of the present disclosure, the sensor module is used to capture color information of an object, and, the captured color information is brought to be compared with pre-stored standard color parameters of a variety of colors. Accordingly, it can recognize directly color of the object to be detected, without requiring provision of the tray and depending on the detection light and the emission light. Accordingly, it not only improves portability but also reduces resource consumption during detection.

It should be noted that, for recognition of color of an object to be detected, assignment of these above functional modules in the color recognition device according to these mentioned embodiments is merely exemplary. In practical application, these functions may be implemented by other different functional modules according to requirements, that is, interior components and/or parts of the color recognition device may be assigned into other different functional modules to implement all or some of the functions. In addition, these embodiments of the color recognition method possess the same concept as these embodiments of the color recognition device, accordingly, details of specific implementation of the color recognition method may refer to those of the specific implementation of the color recognition device, and will not be described here.

It should be understood by those skilled in the art that, all the steps or some of them mentioned in the above embodiments may be implemented, either by hardware(s), or by instructing relevant hardware(s) by program(s) which may be stored in a computer readable storage medium. The mentioned storage medium may be Read-only memory, Disk, CD, and so on.

The above description is merely used to illustrate several exemplary embodiments of the present disclosure, but not to limit the present disclosure. All of changes, equivalent alternatives, modifications, made within principles and spirit of the present invention, should be included within the scope of the present invention.

What is claimed is:

1. A color recognition device, comprising a head portion and a main body portion; wherein:
the head portion has a groove in which a sensor module configured to capture, by virtue of ambient light, color information of an object to be detected is disposed;
the main body portion comprises: a storage module configured for storing standard color parameters of a variety of colors, and a central processing unit configured for comparing color information of the object to be detected with the standard color parameters of the variety of colors stored in the storage module, to recognize color of the object to be detected; and
the groove is provided therein with a light source configured to offer brightness to the object to be detected in a darkroom state which is formed when the groove is in contact with the object to be detected, the light source comprising a standard white-color light source.

2. The device of claim 1, wherein the sensor module comprises an imaging unit, a color filtering unit and a color processing unit;
the imaging unit is configured to perform an imaging process on the object to be detected;
the color filtering unit is configured to separate color in an image of the object to be detected into red, green and blue gray scale brightness; and
the color processing unit is configured to capture values of the gray scale brightness in the image of the object to be detected.

3. The device of claim 2, wherein the imaging unit comprises a lens.

4. The device of claim 2, wherein the color filtering unit comprises a Complementary Metal Oxide Semiconductor (CMOS) sensor.

5. The device of claim 1, wherein the main body portion further comprises a communication module and a power module;
the communication module is configured to transmit the color information of the object to be detected to an upper computer; and
the power module is configured to supply the power to the device.

6. The device of claim 5, wherein the communication module comprises one of a Bluetooth module, a wireless fidelity (Wi Fi) module, an infrared module and a Near Field Communication (NFC) module.

7. The device of claim 5, wherein the power module comprises a battery cell and a power management unit.

8. The device of claim 1, wherein the device further comprises: a standard white board configured to correct the color information of the object to be detected when the object to be detected is in a state of non-darkroom.

9. A color recognition method applied to the color recognition device of claim 1, the method comprising the following steps of:
capturing, by the sensor module, color information of the object to be detected;
judging, by the central processing unit, whether or not there is ambient light in the groove; and
acquiring, by the central processing unit, standard color parameters of a variety of colors pre-stored in the storage module, and, comparing, by the central processing unit, color information of the object to be detected with the standard color parameters of the variety of colors, to obtain a color recognition result.

10. The method of claim 9, wherein the sensor module comprises an imaging unit, a color filtering unit and a color processing unit, and the step of capturing, by the sensor module, color information of the object to be detected, further comprises the following sub-steps of:
performing, by the imaging unit, an imaging process on the object to be detected;
separating, by the color filtering unit, color in an image of the object to be detected into red, green and blue gray scale brightness; and
capturing, by the color processing unit, values of the gray scale brightness in the image of the object to be detected.

11. The method of claim 10, further comprising the following step of:
transmitting, by the communication module, the color recognition result to an upper computer.

12. The method of claim 9, wherein before the step of comparing, by the central processing unit, the color information of the object to be detected with the standard color parameters of the variety of colors, to obtain a color recognition result, the method further comprises the following steps of:
converting, by the central processing unit, the color information of the object to be detected into a digital signal; and
comparing, by the central processing unit, the color information of the object to be detected with the standard color parameters of the variety of colors, to obtain the color recognition result.

13. The method of claim 12, further comprising the following step of:

transmitting, by the communication module, the color recognition result to an upper computer.

14. The method of claim 9, wherein after the step of judging, by the central processing unit, whether or not there is ambient light in the groove, the method further comprises the following steps of:

in response to judging that there is no ambient light in the groove, acquiring, by the central processing unit, standard color parameters of the variety of colors pre-stored in the storage module, and, directly comparing the color information of the object to be detected with the standard color parameters of the variety of colors, to obtain the color recognition result; or in response to judging that there is ambient light in the groove, capturing, by the sensor module, color information of a standard white board in the current condition; correcting, by the central processing unit, the color information of the object to be detected in accordance with the color information of the standard white board; and, comparing, by the central processing unit, the corrected color information with the standard color parameters of the variety of colors, to obtain the color recognition result.

15. The method of claim 14, further comprising the following step of:

transmitting, by the communication module, the color recognition result to an upper computer.

16. The method of claim 9, further comprising the following step of:

transmitting, by the communication module, the color recognition result to an upper computer.

* * * * *